(12) United States Patent
Di Lauro et al.

(10) Patent No.: US 8,992,575 B1
(45) Date of Patent: Mar. 31, 2015

(54) SPINAL IMPLANTS HAVING OFFSETS AND HOOKS

(71) Applicants: Michael Di Lauro, Encinitas, CA (US); Simon Sjovold, North Canton, OH (US)

(72) Inventors: Michael Di Lauro, Encinitas, CA (US); Simon Sjovold, North Canton, OH (US)

(73) Assignee: SeaSpine, Inc., Vista, CA (US)

( * ) Notice: Subject to any disclaimer, the term of this patent is extended or adjusted under 35 U.S.C. 154(b) by 0 days.

(21) Appl. No.: 13/925,211

(22) Filed: Jun. 24, 2013

Related U.S. Application Data

(60) Provisional application No. 61/663,206, filed on Jun. 22, 2012.

(51) Int. Cl.
*A61B 17/70* (2006.01)

(52) U.S. Cl.
CPC ......... *A61B 17/7049* (2013.01); *A61B 17/7056* (2013.01)
USPC .......................................... 606/253; 606/246

(58) Field of Classification Search
USPC ................. 606/246–279, 305–308
See application file for complete search history.

(56) References Cited

U.S. PATENT DOCUMENTS

| | | | |
|---|---|---|---|
| 5,242,445 A | 9/1993 | Ashman | |
| 5,549,607 A | 8/1996 | Olson et al. | |
| 5,601,552 A | 2/1997 | Cotrel | |
| 5,609,592 A | 3/1997 | Brumfield et al. | |
| 5,702,393 A * | 12/1997 | Pfaifer | 606/328 |
| 5,743,911 A | 4/1998 | Cotrel | |
| 6,368,320 B1 * | 4/2002 | Le Couedic et al. | 606/250 |
| 6,413,257 B1 | 7/2002 | Lin et al. | |
| 6,551,318 B1 | 4/2003 | Stahurski | |
| 6,554,832 B2 | 4/2003 | Shluzas | |
| 6,565,565 B1 | 5/2003 | Yuan et al. | |
| 6,626,908 B2 | 9/2003 | Cooper et al. | |
| 6,685,705 B1 * | 2/2004 | Taylor | 606/278 |
| 6,755,830 B2 | 6/2004 | Minfelde et al. | |
| 7,485,132 B1 | 2/2009 | McBride et al. | |
| 7,578,833 B2 | 8/2009 | Bray | |
| 7,704,270 B2 | 4/2010 | De Coninck | |
| 7,850,716 B2 | 12/2010 | Taylor | |
| 7,922,746 B2 | 4/2011 | Miller | |
| 7,959,653 B2 | 6/2011 | Thramann et al. | |
| RE42,545 E | 7/2011 | Ralph et al. | |
| 8,025,680 B2 | 9/2011 | Hayes et al. | |
| 8,029,543 B2 | 10/2011 | Young et al. | |
| 8,029,546 B2 | 10/2011 | Capote et al. | |
| 8,066,743 B2 | 11/2011 | Young et al. | |
| 8,313,516 B2 | 11/2012 | Konieczynski et al. | |
| 8,361,117 B2 | 1/2013 | Michielli et al. | |
| 2006/0200128 A1 | 9/2006 | Mueller | |
| 2009/0036929 A1 | 2/2009 | Reglos et al. | |
| 2009/0204155 A1 * | 8/2009 | Aschmann | 606/264 |
| 2011/0196425 A1 * | 8/2011 | Rezach et al. | 606/278 |
| 2013/0096623 A1 * | 4/2013 | Biedermann et al. | 606/279 |

* cited by examiner

*Primary Examiner* — Jerry Cumberledge
*Assistant Examiner* — Tessa Matthews
(74) *Attorney, Agent, or Firm* — Eva Tan

(57) ABSTRACT

In an embodiment of the invention, for spinal surgery, there is provided an offset arm system that has angular adjustment capability. In an embodiment, there are provided a hook system that is polyaxially or otherwise movably coupled to a body that receives a spinal rod.

7 Claims, 19 Drawing Sheets

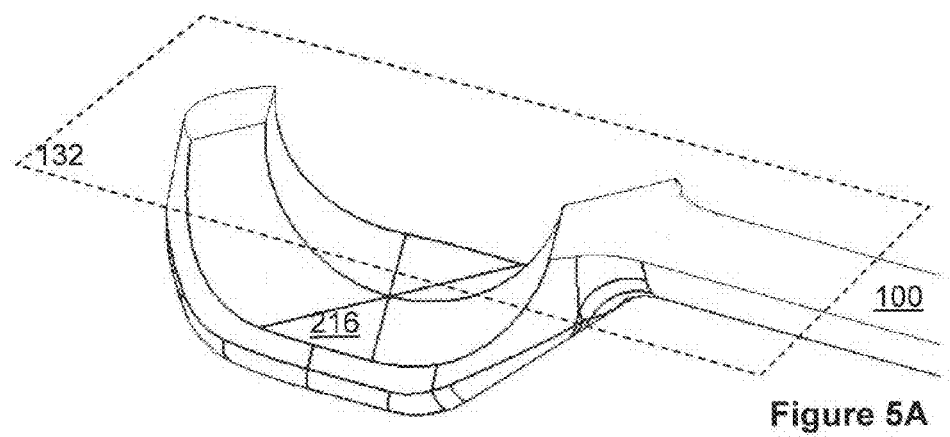
Figure 5A
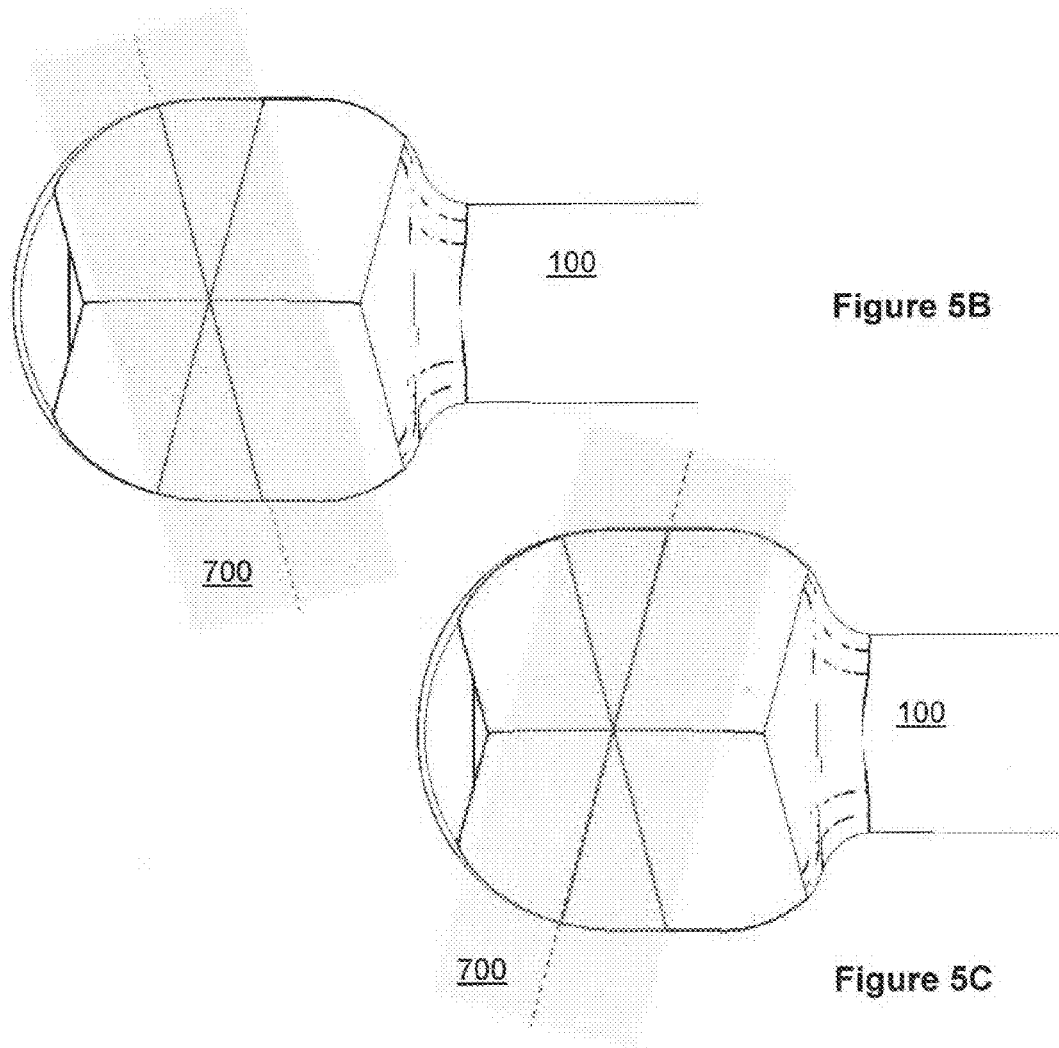
Figure 5B
Figure 5C

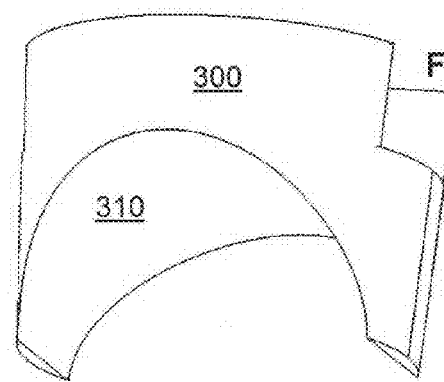
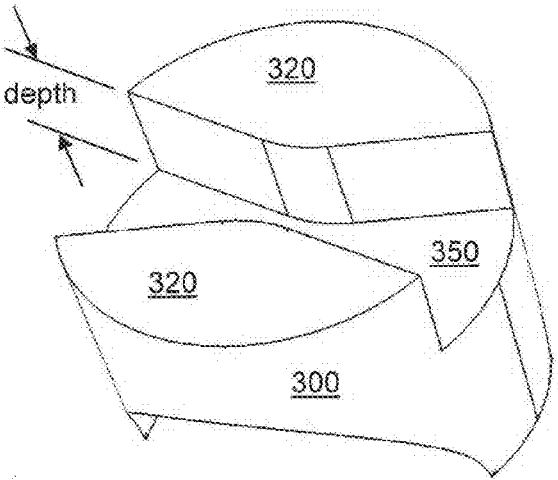
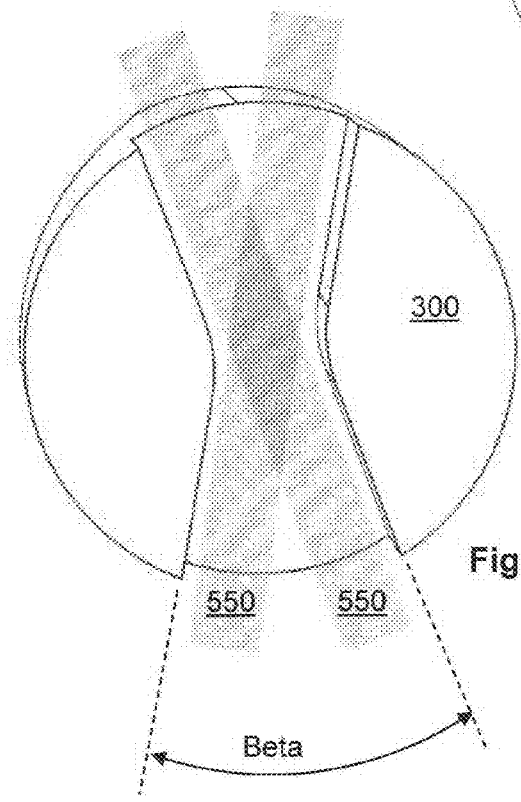
Figure 6A
Figure 6B
Figure 6C

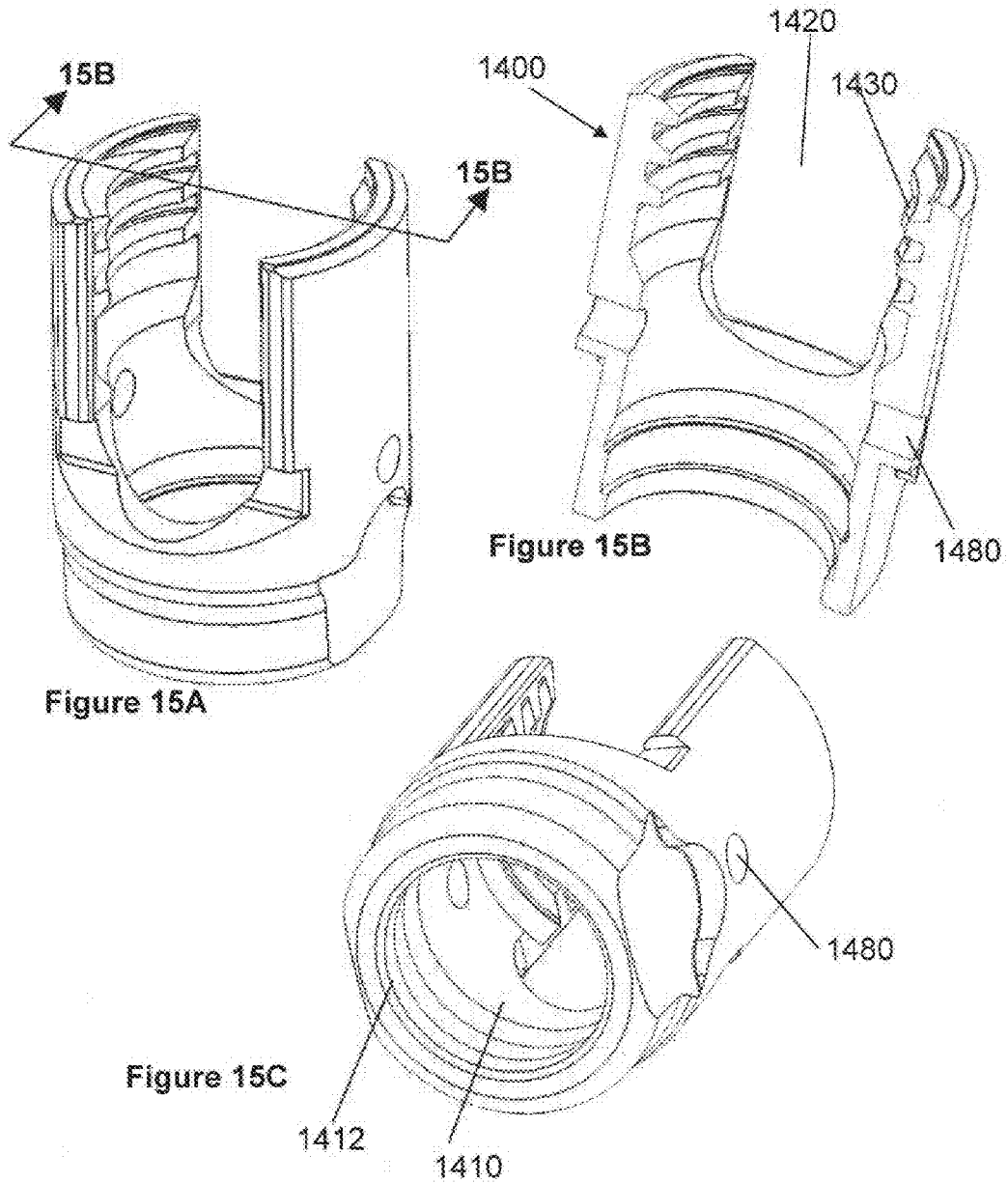

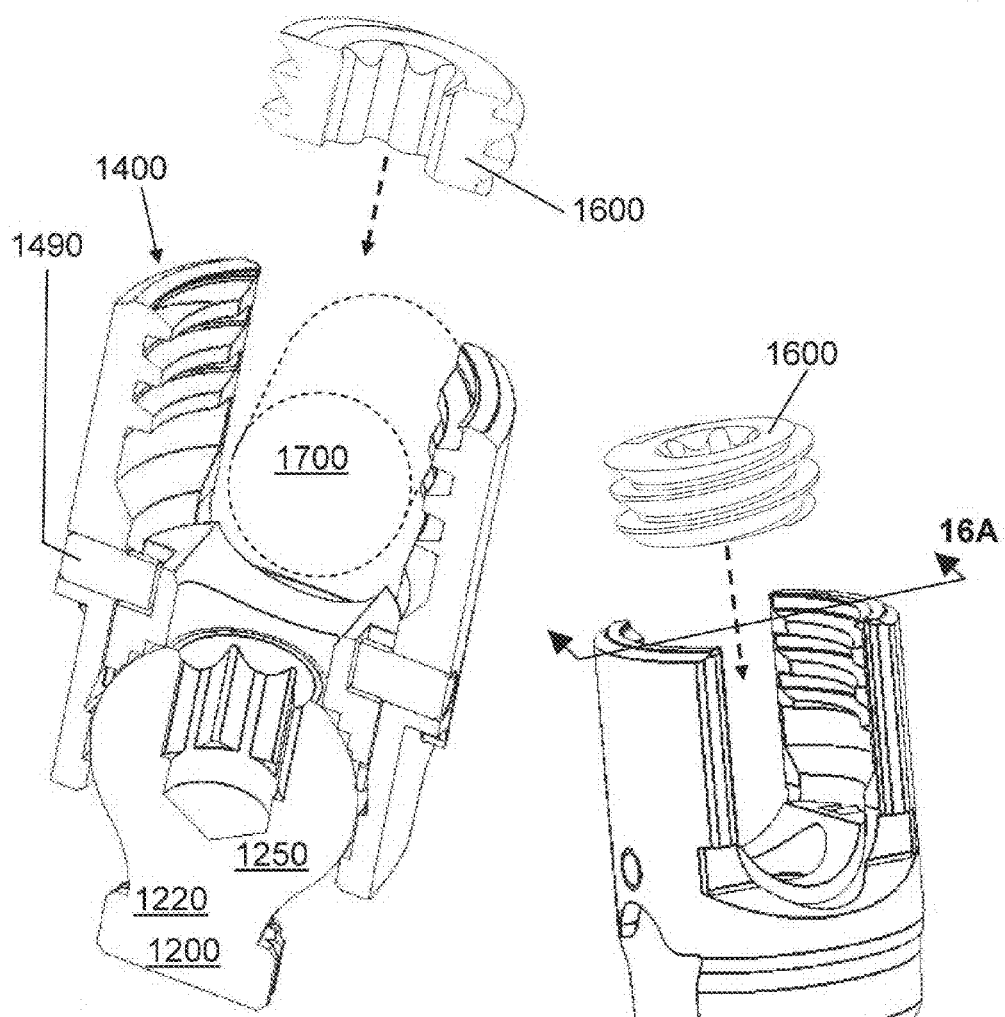
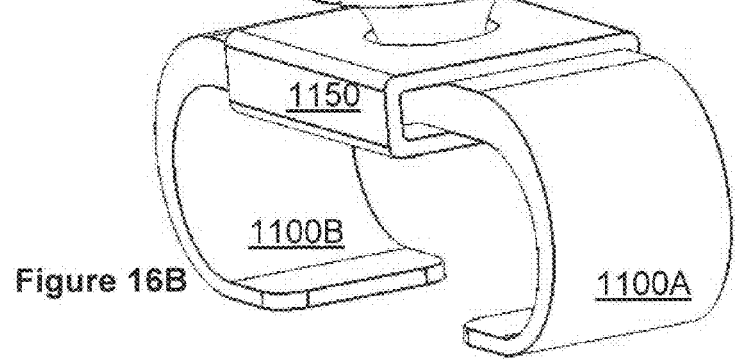
Figure 16A
Figure 16B

SPINAL IMPLANTS HAVING OFFSETS AND HOOKS

PRIORITY

This patent application claims the benefit of provisional U.S. patent application 61/663,206, filed Jun. 22, 2012, which is incorporated herein by reference in its entirely.

TECHNICAL FIELD

This invention pertains to surgery, such as spinal surgery.

BACKGROUND

Spinal surgery aims to achieve stabilization or fusion using a variety of hardware including spacers, rods, screws, hooks and offsets. Improvements in such hardware are desirable to maximize surgeon convenience and patient benefit.

SUMMARY OF THE INVENTION

In an embodiment of the invention, there is provided an offset arm system that provides some angular adjustment capability. Specifically, there may be provided a spinal implant, comprising an arm portion having a lengthwise direction; a body portion joined to or integral with the arm portion, the body portion having a through-hole therethrough and having a blind hole, the blind hole intersecting the through-hole, the blind hole having internal threads; a setscrew having external threads complementary to the internal threads of the blind hole; a spinal rod received in the through-hole; and a saddle element received in the blind hole of the body portion, the saddle element having a vertical axis and being able to rotate around the vertical axis with respect to the body portion, the saddle element contacting the spinal rod and having an underside complementary to the spinal rod, wherein the setscrew urges the saddle element against the spinal rod and the saddle element urges the spinal rod against an internal surface of the through-hole, wherein the through-hole can accept the spinal rod at a range of angles distributed in a horizontal plane, and wherein the saddle element is able to occupy a range of angles around an axis of rotation of the saddle element corresponding to the range of angles of the spinal rod.

In an embodiment, there is provided a pair of cooperating half-hooks that operably interact with a pinion for adjustment and are coupled polyaxially to a body that receives a spinal rod. There may be provided a partially spherical head connected to or integral with the pinion. There may be provided a body that receives the partially spherical head such that in an untightened configuration, the body is able to rotate relative to the partially spherical head around the axis of rotation of the pinion. The coupling between the body and the partially spherical head may be frictional and may provide the ability to retain a position of the body with respect to the hook mechanism at least against the weight of the body.

BRIEF DESCRIPTION OF THE ILLUSTRATIONS

FIG. 5A is a three-dimensional view of a body portion that has been sectioned.

FIG. 5B is view from above of the same body portion, with a spinal rod overlaid at one extreme orientation.

FIG. 5C is view from above of the same body portion, with a spinal rod overlaid at the opposite extreme orientation.

FIG. 6A is a three-dimensional view of the saddle element partially from below.

FIG. 6B is a three-dimensional view of the saddle element partially from above.

FIG. 6C is a view of the saddle element almost directly from above, illustrating possible positions of a control rod relative to the saddle element.

Figure 8A:
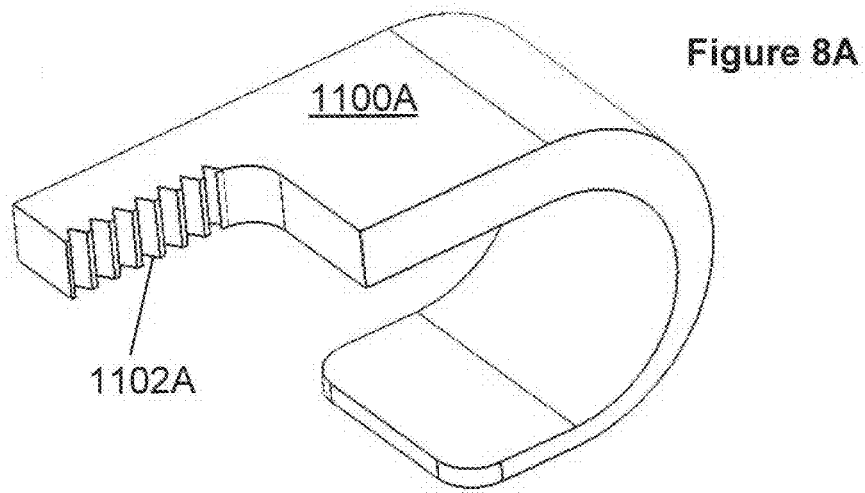

FIG. 8A, tor another embodiment, is a three-dimensional view of a half-hook in isolation.

Figure 8B:
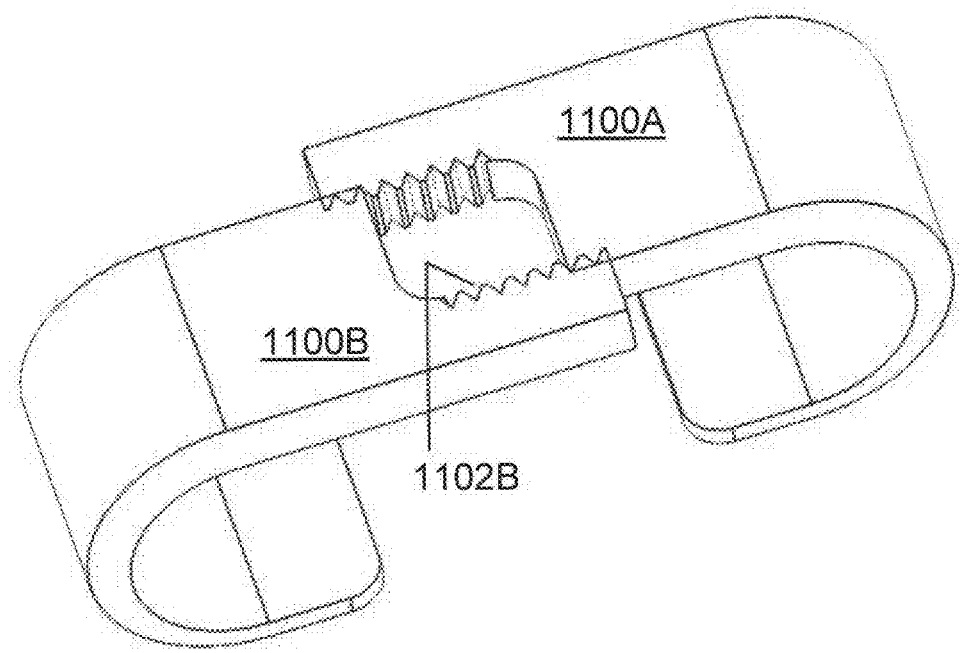

FIG. 8B is a similar view of two half-hooks in isolation.

Figure 9A:
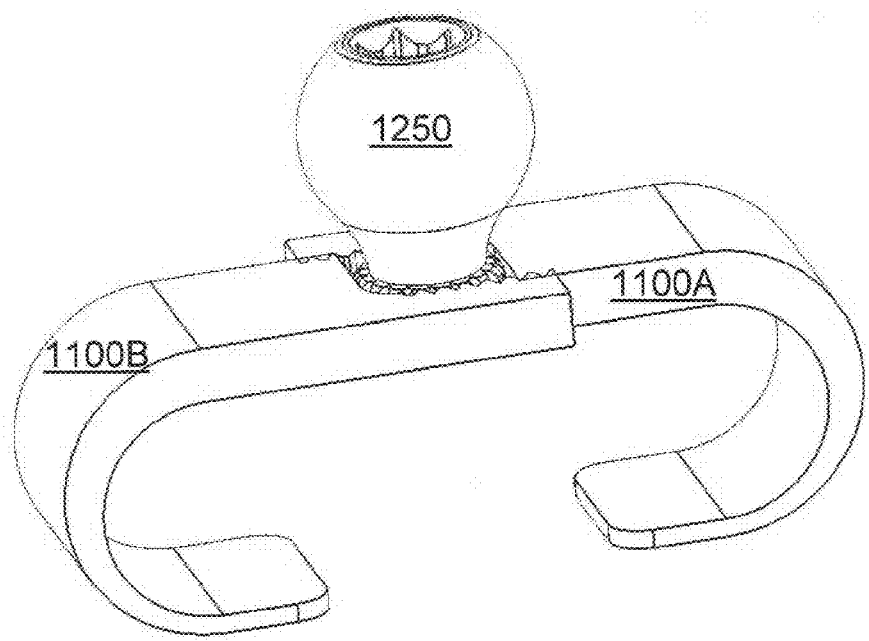

FIG. 9A is a three-dimensional view of two half-hooks, a pinion and a partially spherical head.

Figure 9B:
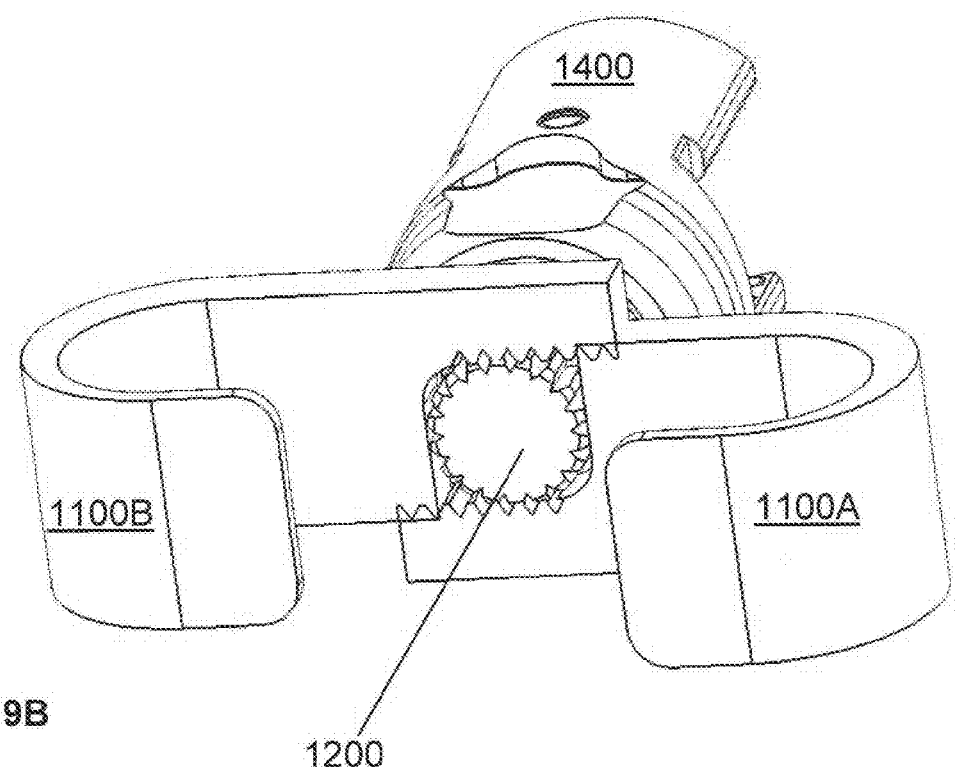

FIG. 9B is a view similar to FIG. 9B but from below.

Figure 10A:
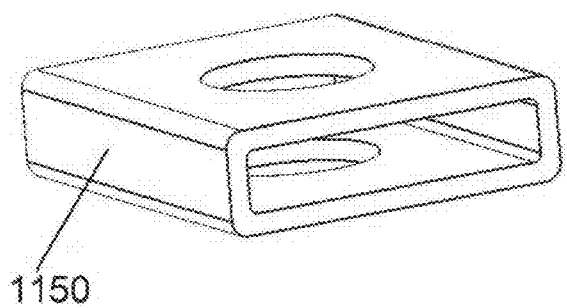

FIG. 10A is a three-dimensional view of the enclosure.

Figure 10B:
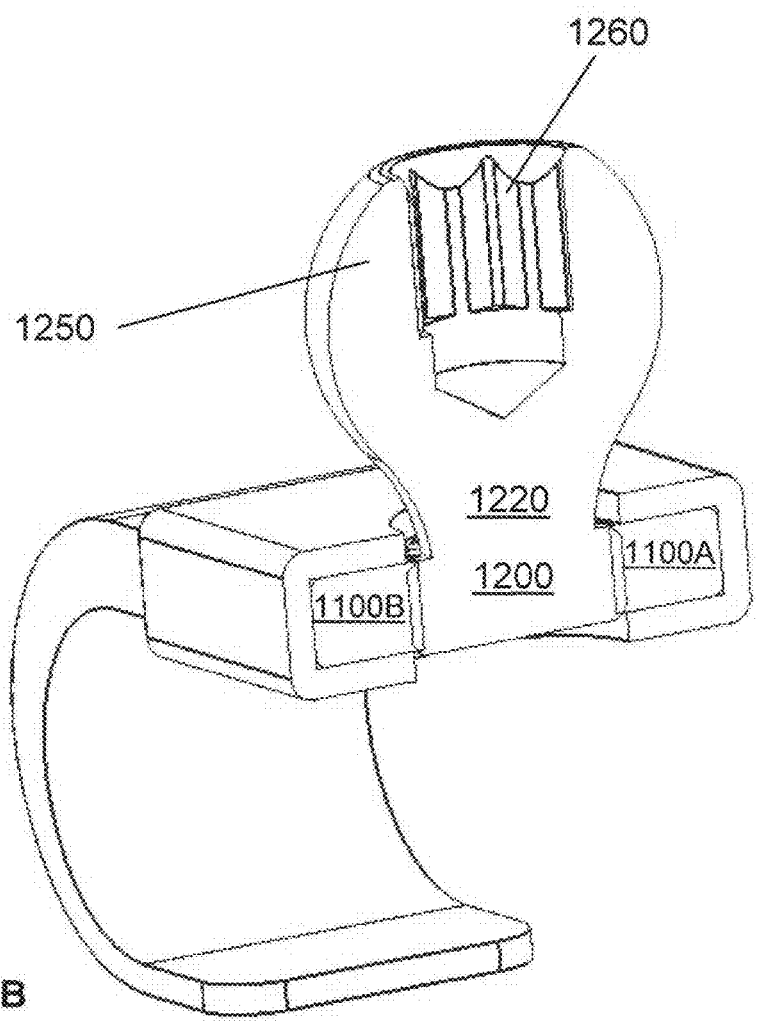

FIG. 10B is a three-dimensional sectional view of the enclosure, the half-hooks, the pinion and the partially spherical head.

Figure 11A:
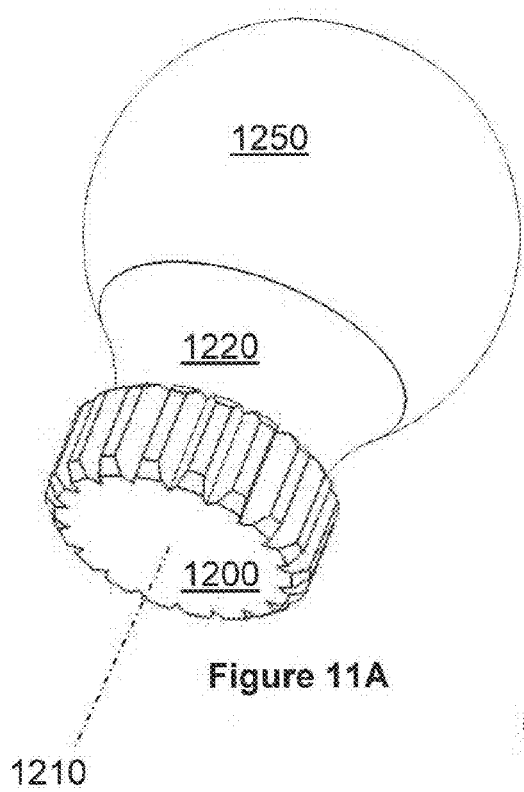

FIG. 11A is a three-dimensional view, somewhat from below, of the pinion and the partially spherical head.

Figure 11B:
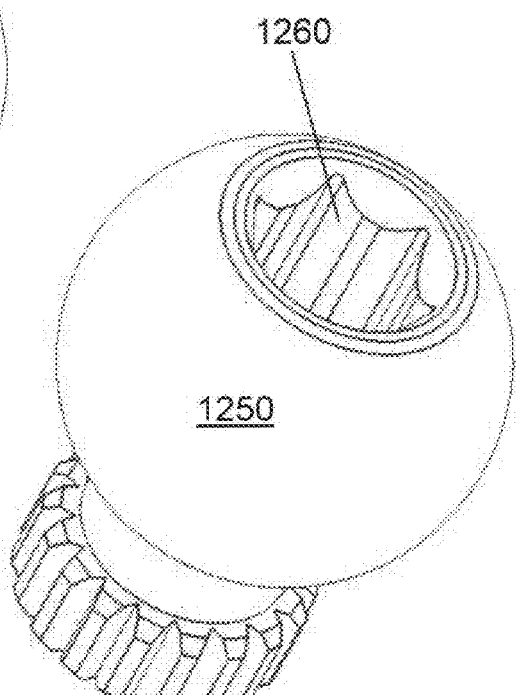

FIG. 11B is a three-dimensional view, somewhat from above, of the pinion and the partially spherical head.

Figure 12:
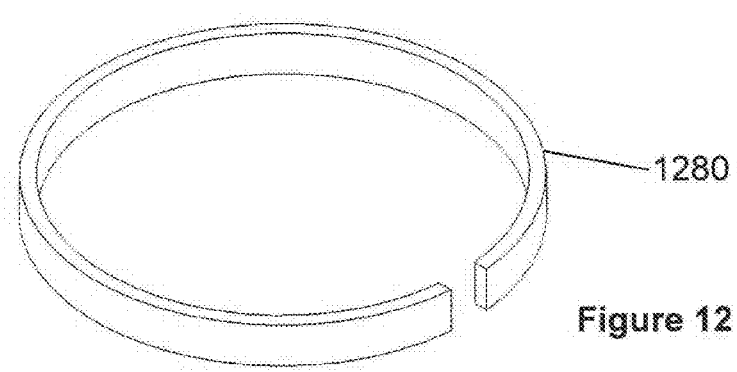

FIG. 12 is a three-dimensional view of the split-ring.

Figure 13A:
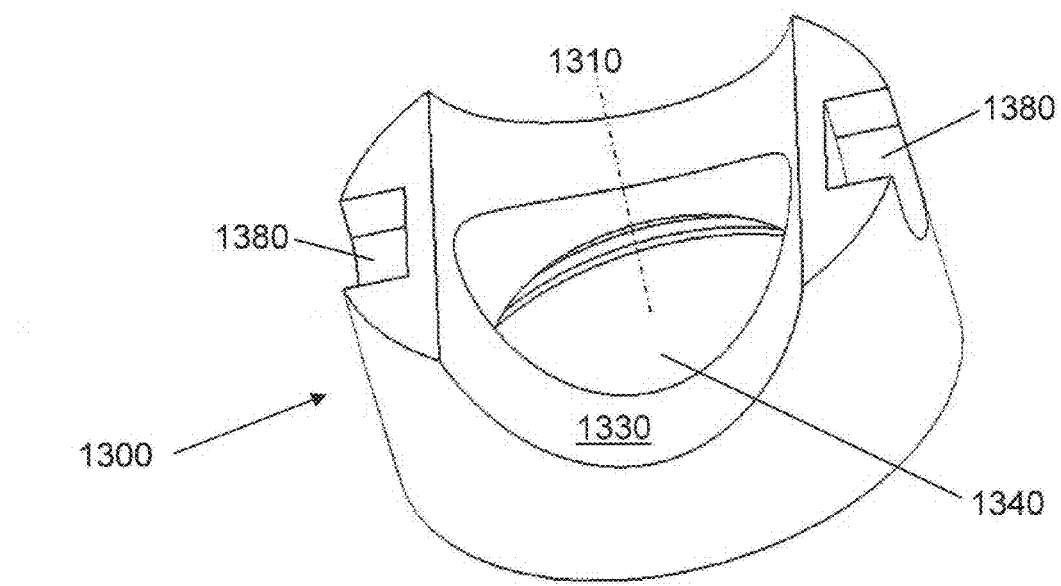

FIG. 13A is a three-dimensional view, somewhat from above, of the saddle.

Figure 13B:
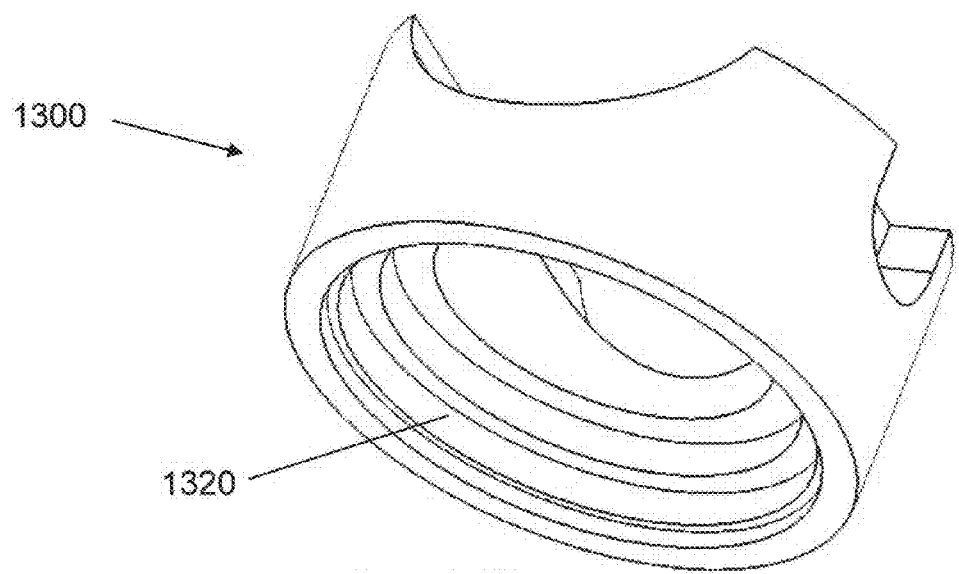

FIG. 13B is a three-dimensional view, somewhat from below, of the saddle.

Figure 14:
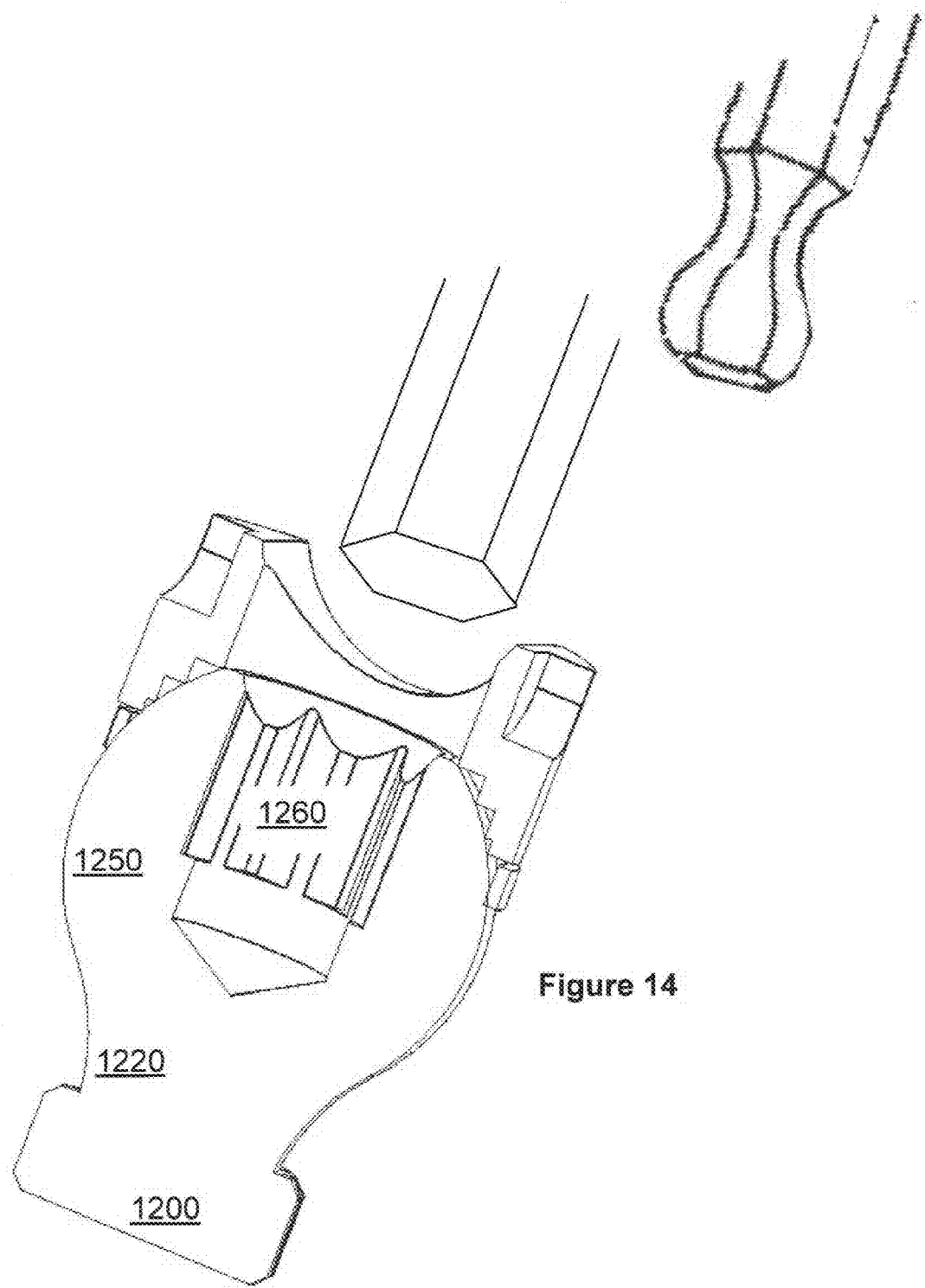

FIG. 14 is a three-dimensional view of a tool being extended through the central hole in the saddle, to the partially spherical head.

FIG. 15A is a three-dimensional view, somewhat from above, of the body.

FIG. 15B is a three-dimensional sectional view of the body.

FIG. 15C is a three-dimensional view, somewhat from below, of the body.

FIG. 16A is a three-dimensional sectioned view of the assembled device, excluding the half-hooks.

FIG. 16B is a three-dimensional view of the assembled device.

Figure 17:
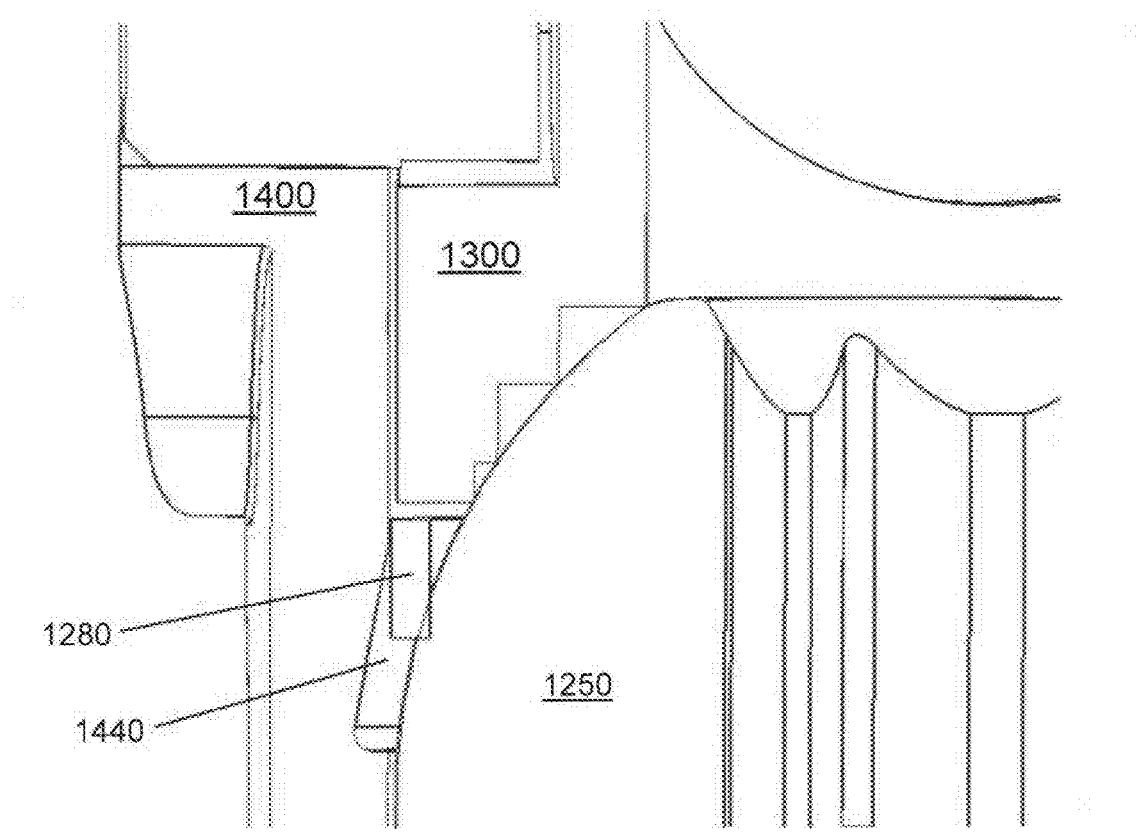

FIG. 17, which is a close-up of FIG. 16A, illustrates the interaction of the split-ring with other components t so as to provide friction.

Figure 18A:
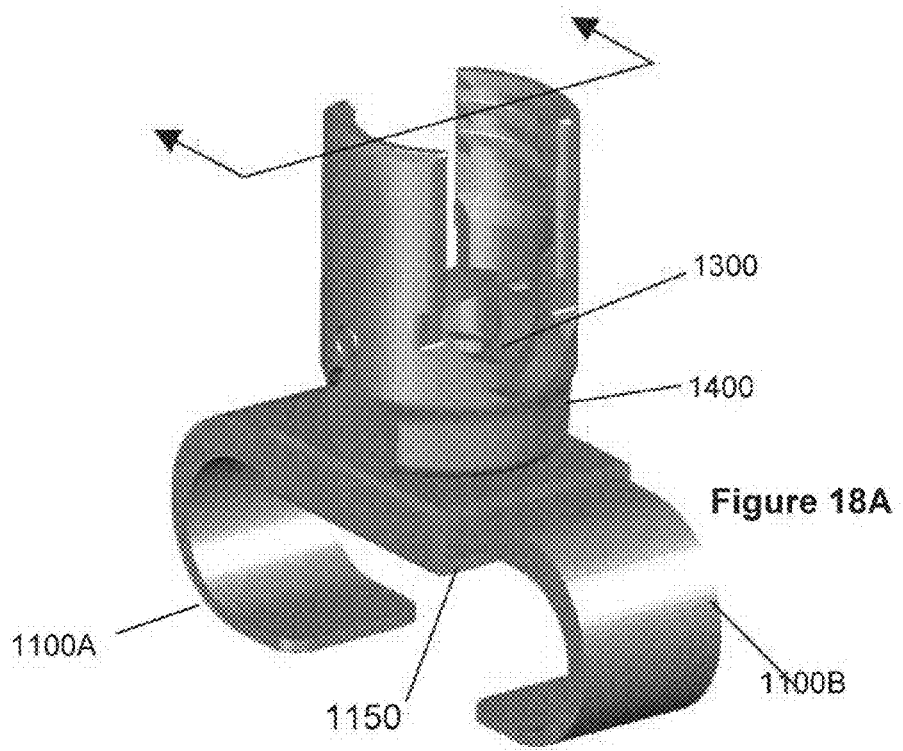

FIG. 18A is a three-dimensional view of an embodiment similar to the embodiment of FIG. 8-17, but having a smaller overall height.

Figure 18B:
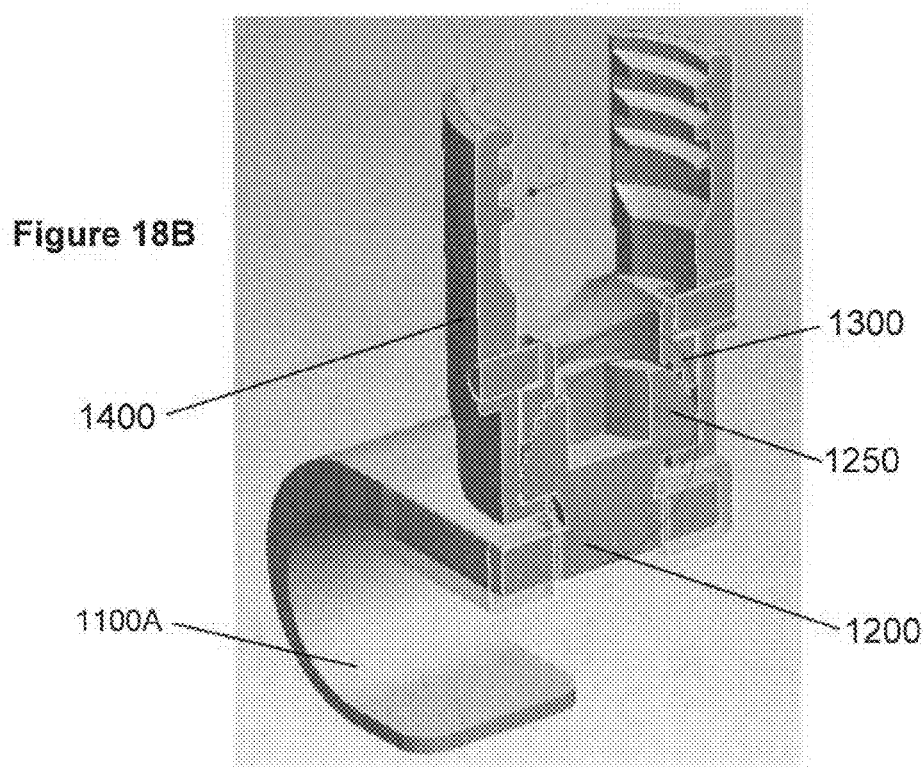

FIG. 18B is a three-dimensional sectional view of FIG. 18.

Figure 19A:
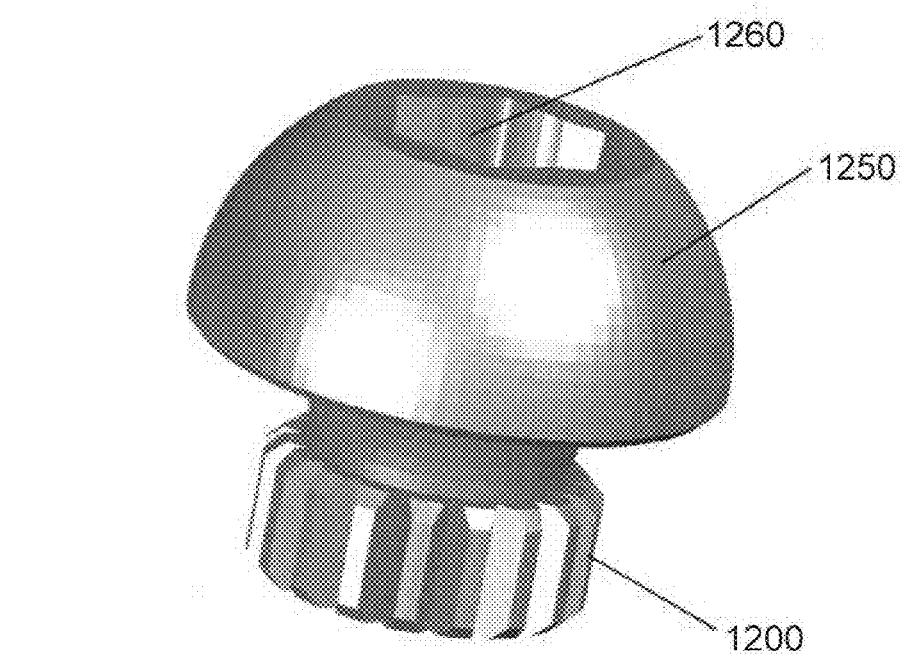
Figure 19B:
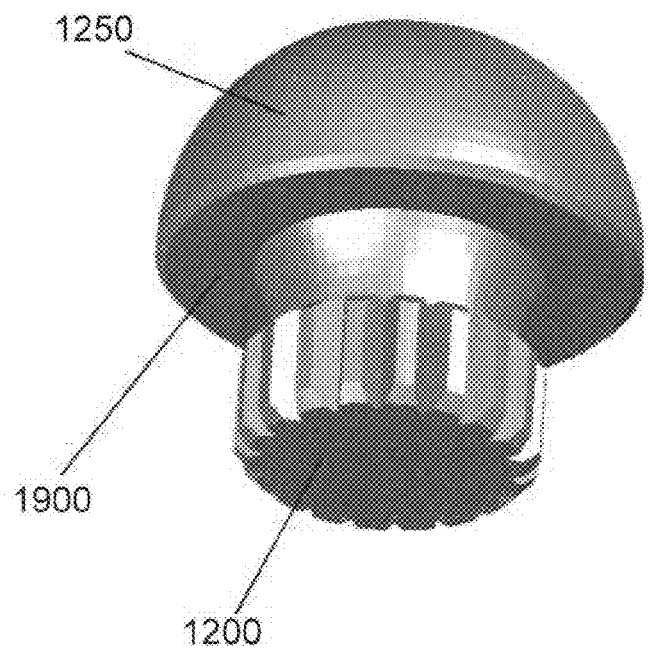

FIGS. 19A and 19B are three-dimensional views, from above and below respectively, of the pinion and partially spherical head.

DETAILED DESCRIPTION

Referring now to FIGS. 1-7, there is illustrated an offset arm system. The offset arm system may, first of all, comprise an arm portion 100. Arm portion 100 may be able to be received in another piece of spinal hardware such as a pedicle screw. As illustrated, arm portion 100 is cylindrical, although it is also possible for arm portion 100 to have cross-sectional shapes other than circular. Arm portion 100 is illustrated as being straight, although other shapes are possible. Arm portion 100 may have a lengthwise direction, which may correspond to a cylindrical axis of the arm portion 100 if arm portion 100 is cylindrical, or, more generally, may correspond to a long dimension of arm portion 100. In turn, arm portion 100 may adjoin or be integral with body portion 200.

Figure 7A:
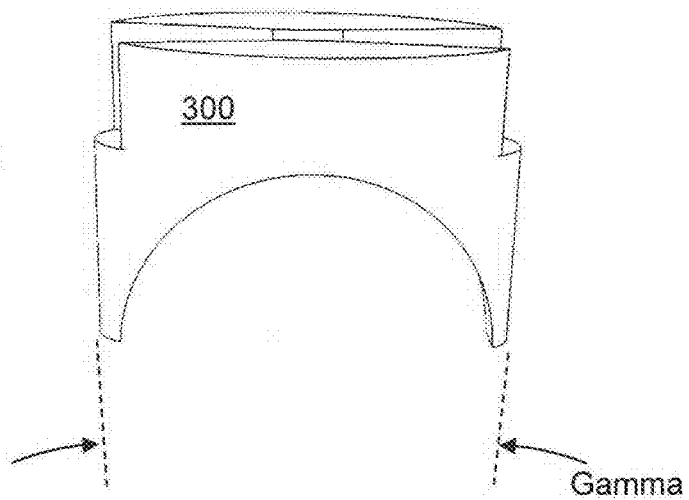
FIG. 7A is a side view of the saddle element, illustrating a particular external taper.
Figure 7B:
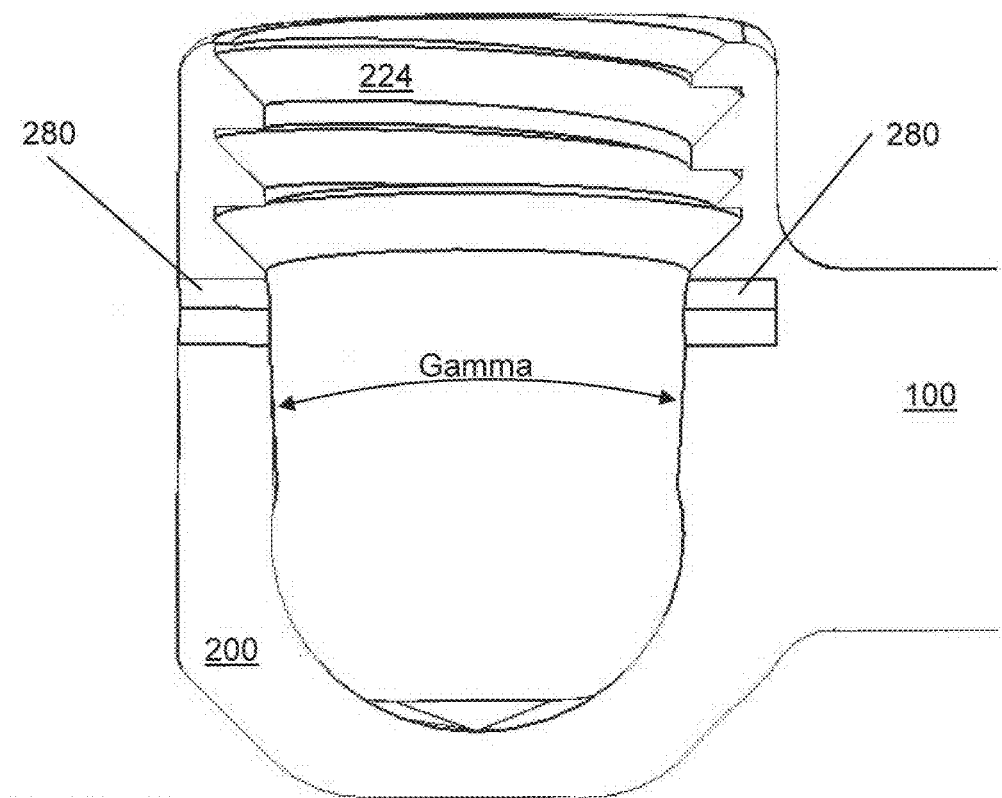
FIG. 7B is a sectional view of the body portion, illustrating a corresponding internal taper.

Referring more particularly to FIGS. 2, 3A-3B and 4A-4B, body portion 200 may have a through-hole 210 therethrough, which may be appropriately dimensioned to receive therein a spinal rod. Body portion 200 may also have a blind hole 220, such that blind bole 220 intersects through-hole 210. Blind hole 220 may have an internal surface that is at least partially internally threaded with internal threads 224, which may be complementary to threads on a setscrew 600. Body portion 200 may also have control rod holes 280 for reception of control rod 550. As illustrated in FIG. 7B, there may be two such control rod holes 280, which may be coaxial with each other. Control rod 550 may be a press fit in at least one of holes 280, or may be otherwise secured to body portion 200.

Figure 1:
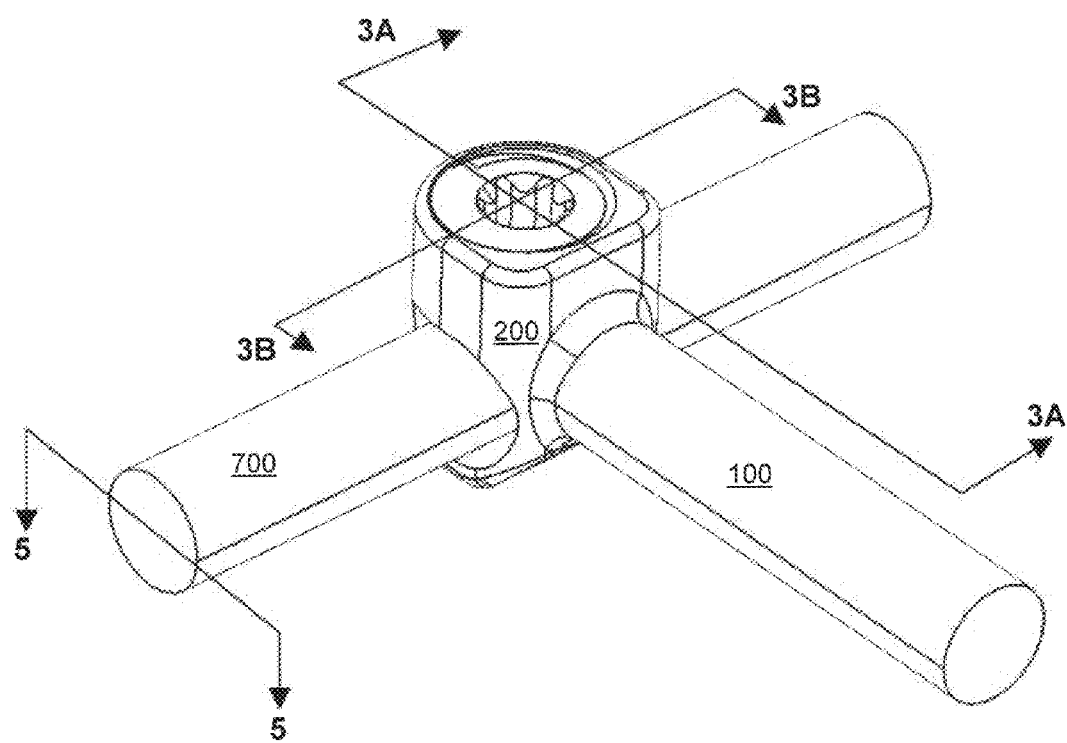
FIG. 1 is a three-dimensional view of an assembled offset arm system.
Figure 2:
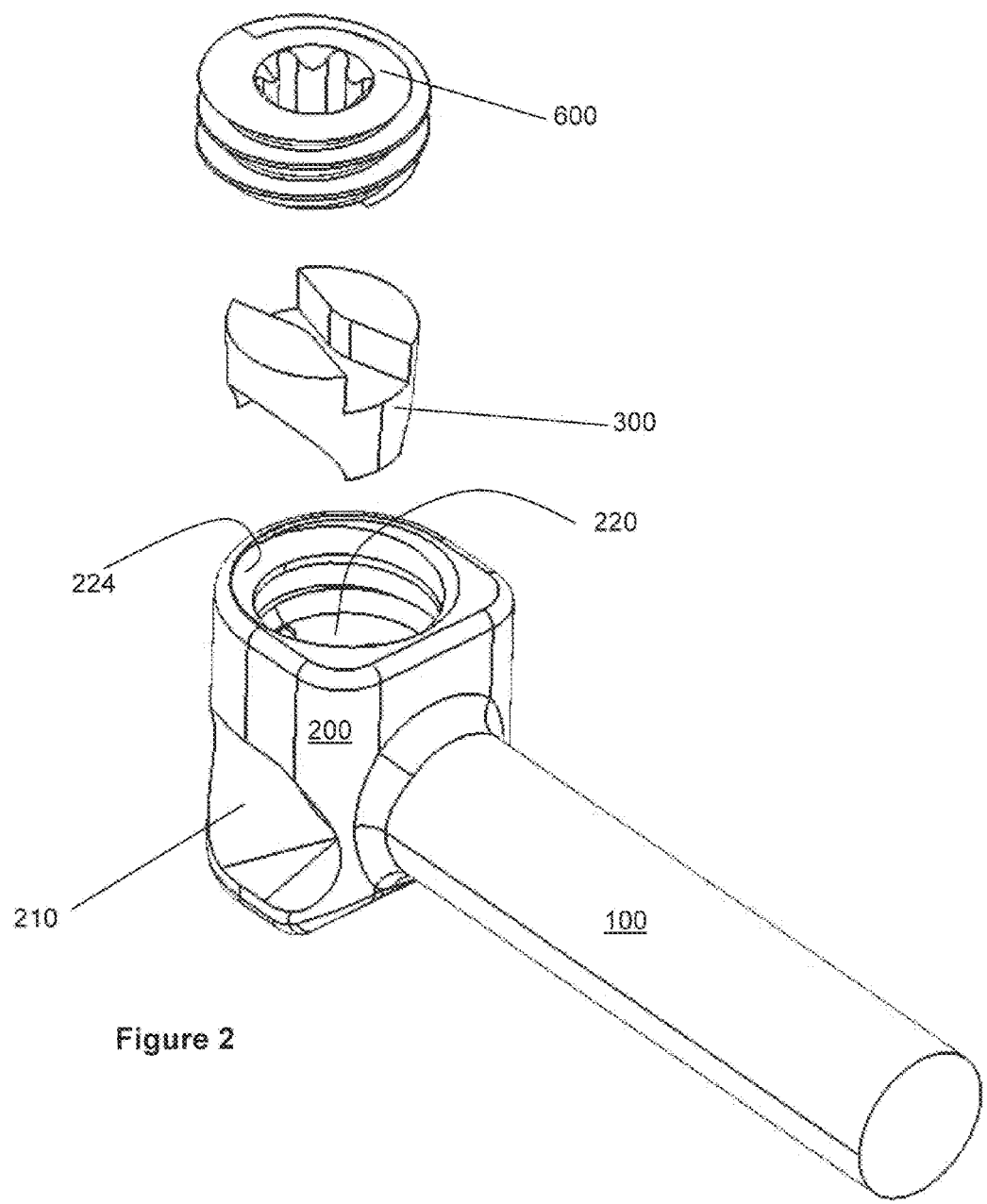
FIG. 2 is a view similar to FIG. 1, but exploded.
Figure 3A:
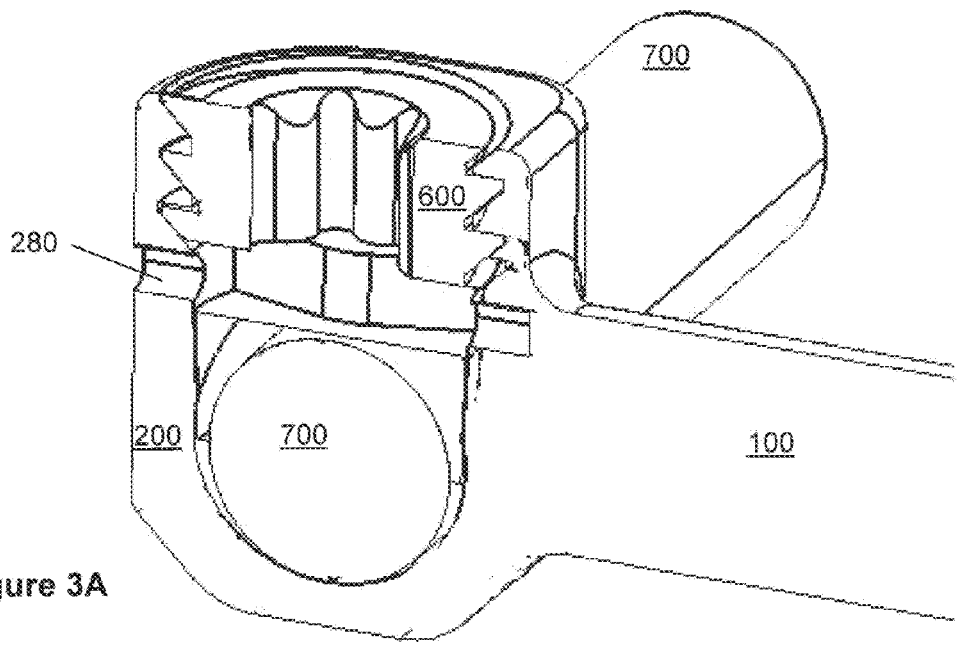
FIG. 3A is a view similar to FIG. 1, but sectioned.
Figure 3B:
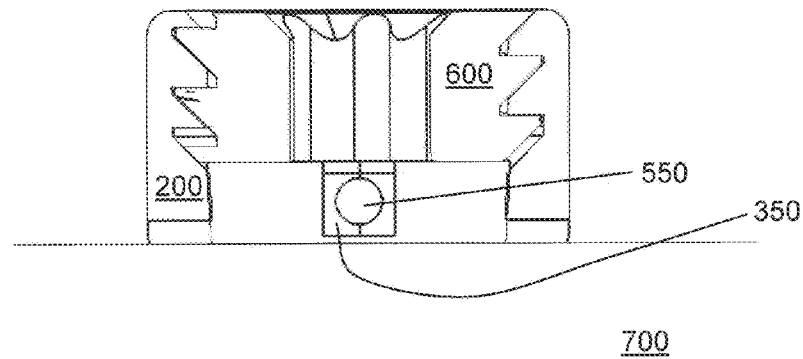
FIG. 3B is a view similar to FIG. 1 but sectioned in a different plane from FIG. 3A.
Figure 4A:
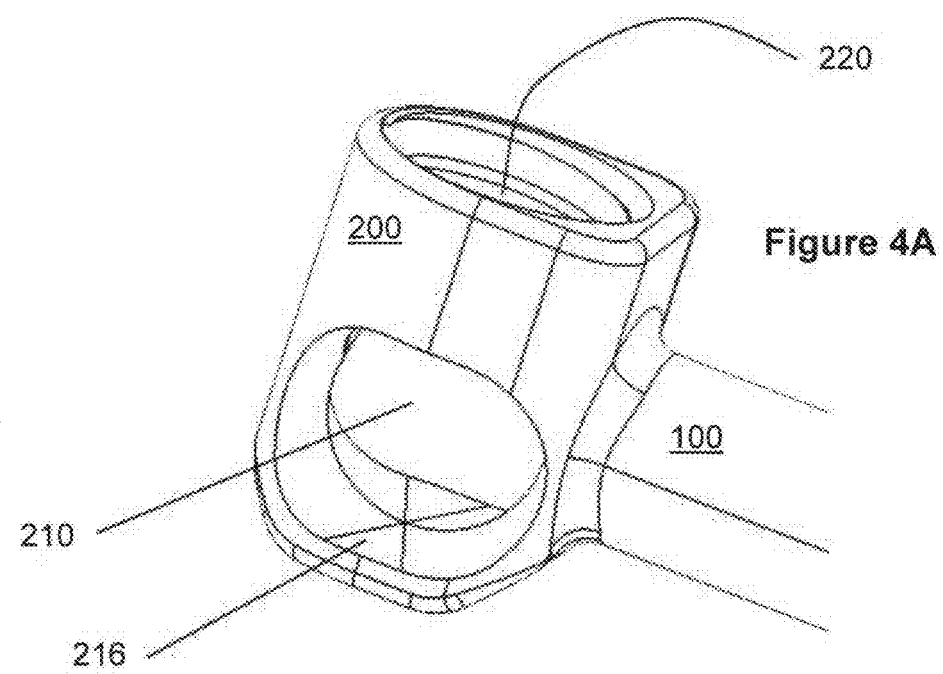
FIG. 4A is a three-dimensional view of the body portion.
Figure 4B:
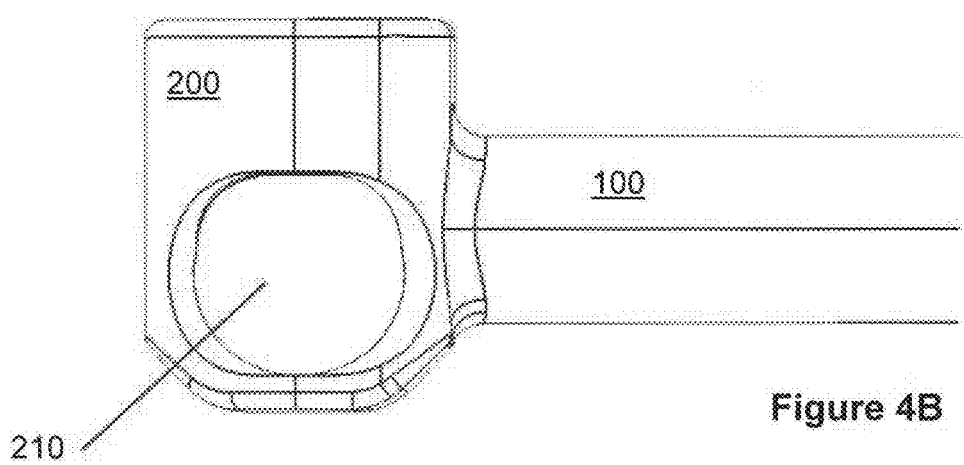
FIG. 4B is a view of the body portion primarily along a principal axis.
Figure 5D:
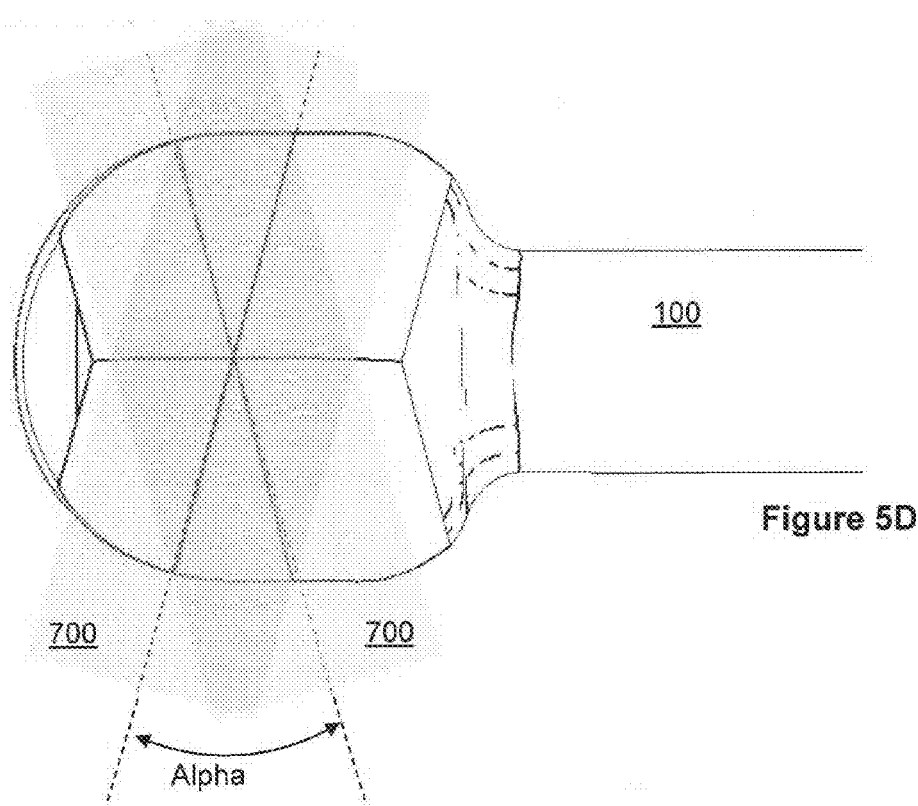
FIG. 5D is an overlay of FIGS. 5B and 5C, with an angle defined.
Figure 5E:
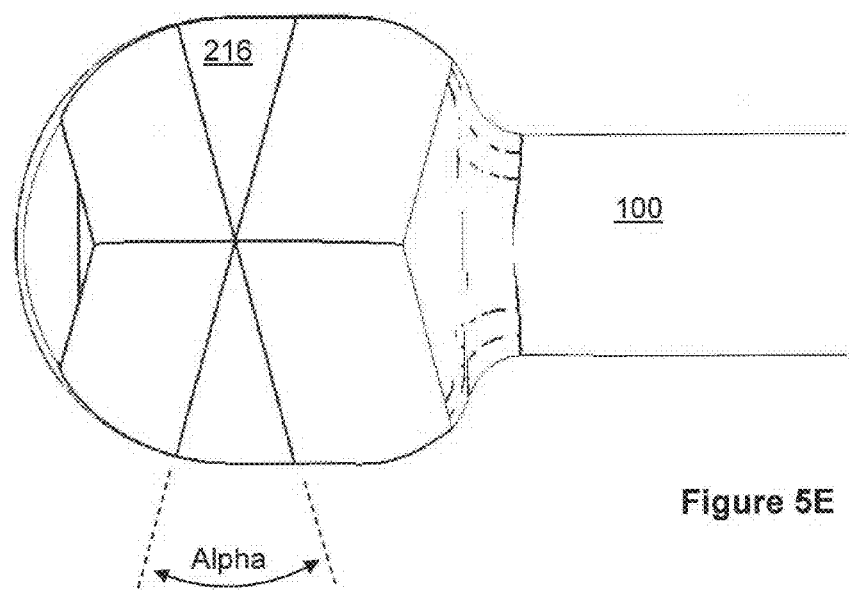
FIG. 5E is similar to FIGS. 5B, 5C and 5D, with an angle defined.

The through-hole 210 through the body portion 200 may be shaped and dimensioned so as to accept within it a spinal rod 700. Spinal rod 700 may be cylindrical. Furthermore, through-hole 210 through the body portion 200 may be shaped and dimensioned such that it has an entrance region and an exit region that permit the spinal rod 700 to pass through through-hole 210 at a variety of orientations, within certain limits. For example, the hole in the body portion 200 through which the spinal rod 700 passes may have a width and angular range and internal shape suitable so that the spinal rod 700 can seat comfortably within it at any angle within the permitted range. Various views of the through-hole 210 are shown in FIGS. 5A-5E. The through-hole 210 may be such as to permit the spinal rod 700 to be oriented through a range of angles in one plane, which may be termed a horizontal plane 132. Through-hole 210 may have, generally along its own hole direction, a narrower central region and it may fan out in either direction away from the central region toward the ends of through-hole 210. It is possible that the bottom surface of through-hole 210 may have a flat region 216 that may be generally triangular. The generally triangular region 216 may have an included angle alpha as labeled in FIG. 5E. The angle alpha may also equal or approximately equal the range of angles of spinal rod 700 that can be accommodated, which is illustrated in FIG. 5D and is also labeled alpha.

The through-hole 210 may be such as to constrain spinal rod 700 to a plane that is horizontal, i.e., allow essentially no range of angular orientation of the spinal rod 700 in a different plane that is orthogonal to the horizontal plane. This is related to the fact that region 216 is flat and may be horizontal, and the underside 310 of saddle element 300 closely fits spinal rod 700 and also may constrain spinal rod 700 to a horizontal plane.

Between the setscrew 600 and the spinal rod 700 there may be a saddle element 300. On its underside 310, the saddle element 300 may have a contour that may complement or at least partially complement the exterior of the spinal rod 700. On its upper side the saddle element 300 may have a top surface 320, which may be flat as illustrated, that can contact the underside of the setscrew 600. The saddle element 300 may be able to change its angular position so as to follow the angular position of the spinal rod 700, by rotating about a vertical axis that is perpendicular to horizontal plane 132. However, in the top surface 320 of the saddle element 300, there may also be a recess 350 such that a control rod 550 may pass within the recess 350. Control rod 550 may serve either or both of two purposes. It may retain the saddle element 300 within the body portion 200 so that when the control rod 550 is in place and the saddle element 300 is within the body portion 200, the saddle element 300 is blocked so as to be unable to pass the control rod 550 and so as to be unable to exit from the body portion 200. At the same time, a portion of the saddle element 300 exists alongside the control rod 550 so that the top surface 320 of the saddle element 300 may contact the setscrew 600. The recess 350 may have a shape that has a relatively narrow central region and fans outward in two opposite directions from the central region. The central region may be wide enough to allow space for control rod 550. The fan regions may have an included angle beta, as illustrated in FIG. 6C. The included angle beta may be at least approximately equal to the included angle alpha associated with through-hole 210. The recess 350 may have a depth that is deeper than the diameter or vertical dimension of the control rod 550.

As a result of this described interaction between control rod 550, recess 350 in saddle element 300, and body portion 200, it is possible that the apparatus may be supplied to the surgeon with the saddle element 300 pre-assembled into the body portion 200 and kept in place there by the control rod 550. Thus, the surgeon may have fewer loose parts that need to be handled during surgery and may therefore have fewer surgical steps that need to be performed during surgery, all of which are beneficial. The control rod 550 may also serve a function of limiting the allowed angular positioning of the saddle element 300 to a certain range. It may be understood that when the spinal rod 700 is in place within the body portion 200, the spinal rod 700 itself encounters limits on its range of angular position due to the spinal rod 700 touching certain surfaces of through-hole 210 or other features of body portion 200 when spinal rod 700 is rotated to certain angular positions. However, when the spinal rod 700 is not present in the body portion 200, it might have been possible for the saddle element 300 to rotate into a position where the saddle element 300 could block entry of the spinal rod 700 into the through-hole 210, rather than permitting entry of the spinal rod 700 into the through-hole 210. It may be useful to guarantee that the anytime the spinal rod 700 approaches the through-hole 210, the spinal rod 700 will be able to pass through the through-hole 210 without potentially being blocked by a saddle element 300 whose angular orientation is non-optimal. Guaranteeing this appropriate alignment can be accomplished as described herein by the interaction of the control rod 550 and the recess 320 in saddle element 300.

The saddle element 300 may have a taper on its exterior, and the internal surface of body portion 200 against which the saddle element 300 bears may have a similar taper, producing a wedging action. The taper may be a Morse Taper. Such tapers may have taper angles that may be equal w each other. In FIGS. 7A and 7B, both tapers are illustrated and are designated as angle gamma. The taper may be such that the saddle element 300 bottoms against the spinal rod 700 before the external taper of the saddle element 300 bottoms against the corresponding internal taper feature of the body portion 200. Any such taper is optional.

In use, when the setscrew 600 is tightened against the saddle element 300 which in turn presses against the spinal rod 700, all components are locked in position. Before such tightening, the spinal rod 700 has the ability to have its angular position chosen or adjusted within certain limits. In the design shown here, the offset arm can sit on the spinal rod at any angle in a range of 30 degrees (approximately 15 degrees to either side of a nominal position). In such adjustment, the bottom of the spinal rod 700 may touch or be tangent to the flat "fan" region 216 of the lower internal surface of through-hole 210. The top of the spinal rod 700 may be cradled by the lower surface 310 of the saddle element 300, and saddle element 300 may rotate as needed with respect to body portion 200.

In a related embodiment, a saddle element 300 may be placed between the body portion 200 and the spinal rod 700. In such an embodiment, the setscrew 600 may bear against the spinal rod 700, which in turn may bear against the saddle element 300, which in turn may bear against the body portion 200.

In another embodiment of the invention, referring now to FIGS. 8-17, there is shown an Adjustable Hook Assembly. In this embodiment, there may be provided a hook assembly that has a polyaxial feature. In such a device, a body capable of gripping a spinal rod may be movably joined to the hook assembly such that relative rotational motion is permitted, within limits, between the hook assembly and the body. Such a joint may involve a partially spherical head that is captured within the body that is capable of gripping the spinal rod.

Referring now to FIGS. 8A-10B, the adjustable hook assembly may comprise two hook halves 1100A, 1100B such that there can he relative motion of the two hook halves relative to each other, such as translational motion. There may be a housing 1150, shown in FIG. 10A, to which both hook halves 1100A, 1100B are slideably coupled, or alternatively the two hook halves 1100A, 1100B may be slideably coupled to each other. Each hook half 1100A, 1100B may comprise a rack 1102A, 1102B.

Each rack 1102A, 1102B may engage a pinion gear 1200. In this configuration, rotation of the pinion gear 1200 can cause one hook half 1100A to translate in a first direction, and cause the other hook half 1100B to translate in the opposite direction. The two opposing hook halves 1100A, 1100B may be slideably coupled to one another or to an assembly that is common to both hook halves 1100A, 1100B. It is possible that hook halves 1100A, 1100B, and also pinion 1200 that they engage with, may be at least partially enclosed by a housing 1150, as illustrated in FIGS. 10A-10B.

Referring now to FIGS. 11A-11B, it is further illustrated that the pinion 1200 may be connected to or integral with a partially spherical head 1250. which may comprise a portion of a sphere. Between partially spherical head 1250 and pinion 1200 may be a transition region that may be referred to as neck 1220. Partially spherical head 1250 may have a center, which may be located coincident with the axis of rotation 1210 of pinion 1200. Partially spherical head 1250 may have, at or near its top, a tool interface 1260 suitable to receive a tool capable of transmitting torque to partially spherical head 1250. The tool interface 1260 may, for example, be an internal hex interface or similar interface as is known in the art. The corresponding tool could be a simple hex wrench (Allen wrench) or could be a ball end hex wrench, which would allow approach to the tool interfaced 1260 from more angles than simply along the axis of pinion 1200. Both are illustrated in FIG. 14.

Partially spherical head 1250 may be suitable to be received within another component of spinal hardware. For example, the presence of spherical shape of partially spherical head 1250 may allow the adjustable hook assembly to connect with other spinal hardware at a variety of angular orientations, thereby providing the assembly with the ability to adjust in at least one degree of freedom. Such adjustability may be polyaxial.

Referring now to FIG. 12, there may further he provided a split ring 1280, as discussed elsewhere herein. Split ring 1280 may have a shape that forms a substantially large portion of a substantially circular, except for a gap in one place. The dimensions of the substantially circular shape may be coordinated with appropriate dimensions of partially spherical head 1250 and body 1400 as desired. The cross-sectional shape of split ring 1280 may be rectangular as illustrated, although other cross-sectional shapes are also possible.

Referring now to FIGS. 13A-13B, there may further be provided a saddle 1300. Saddle 1300 may have an axis of symmetry 1310 such that at least some of the features of saddle 1300 may be axisymmetric around that axis. Saddle 1300 may have an underside 1320 that is at least approximately spherical in a manner that is complementary to partially spherical head 1250. As illustrated, the underside of saddle 1300 does not have to be smooth, but rather may comprise grooves or sharp edges. Such grooves or sharp edges may bear against the corresponding surface of partially spherical head 1250 for purposes of enhancing grip or friction when the assembly is in a tightened state. On the upper side of saddle 1300, there may be provided a curved recess 1330, which may be cylindrical or at least partially cylindrical. Curved recess 1330 may be complementary in shape and dimension to a spinal rod. Curved recess 1330 may have a cylindrical axis, which may intersect and be perpendicular to axis of symmetry 1310. The curved recess 1330 is illustrated as being smooth, although it could alternatively comprise gripping features such as roughness. Saddle 1300 may have a central hole 1340 therethrough, whose axis may coincide with the axis of symmetry 1310 of saddle 1300. With reference to FIG. 14, central hole 1340 may allow access of a tool to the tool interface 1260 that may be present in partially spherical head 1250. Specifically, central hole 1340 through saddle 1300 may be larger than the maximum transverse dimension of the tool, and may be larger by a sufficient amount so as to allow the tool to approach tool interface 1260 from more directions than just along the axis of symmetry 1310 of saddle 1300. Further, saddle 1300 may have one or more (two are illustrated) retention features 1380. These retention features 1380 are illustrated as being small cutouts that can receive a retention pin 1490 described elsewhere herein.

Referring now to FIGS. 15A-15C, there may further be provided a body 1400. The body 1400 may have a through-hole 1410 therethrough. The through-hole 1410 may be of sufficient diameter to allow the pinion 1200 to pass through the through-hole 1410, but the partially spherical head 1250 may have a diameter larger than the diameter of the through-hole 1410. The body 1400 may further comprise a slot 1420. which may be generally U-shaped, opening toward the proximal end of body 1400, and may be suitable to receive a spinal rod. Through-hole 1410 may comprise threads 1430 suitable to receive a setscrew 1600. Such threads 1430 may be interrupted by the slot 1420. On its interior at the lower end, the body 1400 may comprise one or more ridges or some form of roughness. Such features may help to grip and lock the position of the partially spherical head 1250 when the entire assembly is in a tightened configuration. The body 1400 may further comprise one or more (two are illustrated) retention holes 1480 in the wall of body 1400, and retention hole(s) 1480 may in turn receive retention pins 1490. Retention pin(s) 1490 may be such as to block passage of saddle 1300 past retention pin(s) 1490 when retention pin 1490 is present in the illustrated position. As such, the assembly may stay together as a single assembly, hut in the absence of tightening of setscrew 1600 against a spinal rod 1700, there may be some permitted motion of partially spherical head 1250 relative to body 1400.

The assembly may also include a setscrew 1600 that may interface with internal threads 1430 in body 1400. The assembly may also include a spinal rod 1700 that may be gripped within the body 1400 between setscrew 1600 and saddle 1300. Tightening setscrew 1600 may bear against spinal rod 1700, which in turn may bear against saddle 1300. Such tightening of setscrew 1600 may result in a lightened configuration of the implant.

When the assembly is in an untightened configuration, the partially spherical head 1250 may be able to rotate with respect to body 1400 and thereby cause translation of hook halves 1100A, 1100B. Such translation may cause hook halves 1100A, 1100B to come closer to each other or further apart from each other. One direction of such motion may establish or tighten a grip of the hook assembly on a body pan. The other direction of such motion may release or loosen the grip of the hook assembly on the body part.

Split ring 1280 may be dimensioned, and may be dimensioned in conjunction with appropriate dimensions of saddle 1300 and body 1400, so that even when the assembly is not tightened (such as by the presence of a spinal rod and a setscrew), some friction is maintained. For example, such friction may be appropriate so that whatever orientation body 1400 is set to relative to partially spherical head 1250, it will remain in that orientation against slight applied force or torque, such as the weight of body 1400; but when an appropriate larger amount of, force or torque is applied, the orientation of body 1400 can be changed relative to partially spherical head 1250. It is also possible that in the described untightened situation (setscrew 1600 absent or present but untightened), it may be possible to rotate partially spherical head 1250 relative to body 1400. This rotation may be performed against a modest amount of friction resulting from the interaction of split ring 1280 with other components. Of course, it would also be possible to rotate partially spherical head 1250 by rotating body 1400 in unison with partially spherical head 1250, if desired and if convenient. Split ring 1280 may have a cross-sectional shape that is substantially rectangular, while the overall shape of split-ring 1280 may be generally the shape of a circle with a slight gap missing. More specifically, the cross-sectional shape may be rectangular with an axial dimension that is larger than the thickness of the split-ring 1280 in the plante of split-ring 1280. It is possible that the natural shape of such a split ring can be a portion of a cylinder (except for the gap). Deformation to provide friction could occur due to spreading-apart of the gap of split-ring 1280. Alternatively, deformation to provide friction could occur due to deformation of split-ring 1280 such that the lower edge of the split-ring is forced out to a larger radial location than the radial location of the top edge of the split-ring, resulting in the split-ring being deformed a frusto-conical shape. Furthermore, deformation to provide friction could be any combination of those types of deformation. The body 1400 may have an internal recess 1440 that may provide space into which the split-ring 1280 may deform or expand. The partially spherical head 1250 may contact a lower internal corner of the split-ring 1280 and the body 1400 may contact the split-ring 1280 an upper portion of split-ring 1280, such as above a midplane of the split-ring 1280. It is also possible that saddle 1300 may push vertically downward on split-ring 1280. Frictional gripping could occur due to spreading-apart of the gap of split-ring 1280. Alternatively, frictional gripping could occur due to deformation of split-ring 1280 such that split-ring is deformed from a cylindrical shape to a frusto-conical shape. Furthermore, frictional gripping could occur by any combination of those types of deformation.

After complete assembly of all spinal hardware inside the body of a patient, and specifically the installation of setscrew 1600, the hardware may be tightened so as to either directly or indirectly exert force on partially spherical head 1250. Such tightening may not only fix the angular position of the hook assembly relative to the other hardware in regard to angulation and translation, but it may also fix the rotational position of the pinion 1200, so that there is no longer any possibility of opening or closing the hook assembly or loosening or tightening the grip of the hook assembly.

Rotation of the spherical ball head clockwise or counter-clockwise, relative to housing 1150, can move the half-hooks 1100A, 1100B either towards each other or away from each other. It is possible that when the body 1400 receives a spinal rod 1700 and the spinal rod 1700 is locked in place such as by a setscrew 1600, the spinal rod 1700 may bear indirectly (through saddle 1300) against the partially spherical head 1250 thereby locking the partially spherical head 1250 in place relative to the body 1400.

It is further possible that the adjustable hook assembly may comprise a ratchet that may influence the opening or closing or both of the hook assembly even when the partially spherical head 1250 is not locked into additional spinal hardware. For example, the ratchet may permit the hook halves to he drawn closer to each other while not permitting the hook halves 1100A, 1100B to spread apart from each other. It is possible that a linear ratchet could be associated with the linear motion of one or both of the hook halves 1100A, 1100B. It is possible that a rotary ratchet could be associated with the rotation of pinion 1200 or of a shaft or other component associated with pinion 1200. Any type of ratchet could be releasable so that motion in a direction not ordinarily permitted by the ratchet would be possible if the ratchet is released.

All of the described components may be pre-assembled. Pre-assembly may be such as to create a desired amount of friction so that the body 1400 will maintain a desired position with respect to the partially spherical head 1250. A possible assembly technique may involve starting with the body 1400, then inserting the pinion 1200 until the bottom of the partially spherical head 1250 bottoms out against the interior surfaces of body 1400, then inserting the split ring 1280, then inserting the saddle 1300 so that the saddle 1300 is in loose contact with at least some other components (either the partially spherical head 1250 or the split ring 1280), and then capturing the saddle 1300 in place by installing the retention pin(s) 1490.

There can be a polyaxial relationship between the housing and the partially spherical head 1250. Alternatively, it is possible that permitted motion could be less than fully polyaxial. The opening (through-hole) 1412 in the lower part of the body 1400, which is part of through-hole 1410, is illustrated as being circular, but it does not have to be perfectly circular. Instead, it could be shaped so as to allow the connecting neck 1120 between the pinion 1200 and the partially spherical head 1250 to angulate through a certain amount of angulation in a first direction and a different amount of angulation in a different direction such as a second direction that is perpendicular to the first direction. For example, there could be permitted relative motion but in some direction or directions that motion could be constrained, such as to a uniplanar motion.

Housing 1150 is illustrated herein, but it is possible that other designs could be used to provide appropriate mechanical connection between half-hooks 1100A, 1100B and pinion 1200 and other parts as needed.

It is also possible that any such device could provide a slight amount of translational adjustment in a direction that is perpendicular to axis of rotation 1210. For example, the hole in housing 1150 through which neck 1220 passes could be somewhat larger than the actual diameter of neck 1220, or could be a non-circular shape. The internal dimensions of housing 1150 could provide some space for half-hooks 1100A, 1100B and pinion 1200 to move slightly (small enough distances to avoid disengagement of pinion 1200 from racks 1102A, 1102B).

Yet another embodiment is illustrated in FIGS. 18A, 18B and 19. In this embodiment, the total height of the device may be smaller than it is for the design illustrated in FIGS. 8-17. Having a smaller total height may reduce possible visible protrusion of the device in the skin of the patient. In this embodiment, the partially spherical head 1250 may have an underside 1900 that is substantially flat. Underside 1900 may, for example, be substantially parallel to a surface of housing 1150. In this situation, body 1400 may have a bottom that wraps around the underside of partially spherical head 1250. It can be appreciated that a design as illustrated in FIGS. 18A-19 would not have a polyaxial adjustment ability, or would not have nearly as much polyaxial adjustment ability as the previous embodiment. However, such embodiment would still have the ability for body 1400 to rotate with respect to partially spherical head 1250 around an axis that may coincide with the axis of rotation of pinion 1200.

Finally, it can also be appreciated that in still other designs, if there is an underside 1900 that is substantially flat as illustrated in FIG. 19, what is shown as the top of partially spherical head 1250 could instead be a non-spherical shape such as flat. This could result in a head having a disc shape instead of a partially spherical shape. Corresponding design changes could be made to saddle 1300.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases respectively, as set forth in the United States Patent Office Manual of Patent Examining Procedures, Section 2111.03.

All documents referred to herein are incorporated by reference in their entirety.

We claim:

1. A spinal implant, comprising;
an arm portion having a lengthwise direction;
a body portion joined to or integral with said arm portion, said body portion having a through-hole therethrough and having a blind hole, said blind hole intersecting said through-hole, said blind hole having internal, threads;
a setscrew having external threads complementary to said internal threads of said blind hole;
a spinal rod received in said through-hole; and
a saddle element received in said blind hole of said body portion, said saddle element having a vertical axis and being able to rotate around said vertical axis with respect to said body portion, said saddle element contacting said spinal rod and having an underside complementary or at least partially complementary to said spinal rod,
wherein said setscrew urges said saddle element against said spinal rod and said saddle element urges said spinal rod against an internal surface of said through-hole,
wherein said through-hole can accept said spinal rod at a range of angles distributed in a horizontal plane, and
wherein said saddle element is able to occupy a range of angles around said vertical axis of said saddle element corresponding to said range of angles of said spinal rod,
wherein said saddle element comprises a recess in a top surface of said saddle element, said recess having a depth from said top surface,
wherein said implant comprises a control rod secured to said body portion and fitting within said recess in said saddle element, wherein said control rod cooperates with an internal shape of said recess to limit rotation of said saddle element about said vertical axis with respect to said body portion to a range of angles.

2. The implant of claim 1, wherein said control rod has a diameter that is smaller than said depth of said recess.

3. The implant of claim 1, wherein said range of angles determined by said control rod and said recess is substantially equal to said range of angles in which said spinal rod can be received in said through-hole.

4. The implant of claim 1, wherein said through-hole has a wider region transitioning to a narrower central region followed by a wider external region, and has on its bottom surface a flat region.

5. The implant of claim 1, wherein said saddle element has an exterior having an external taper and said body portion has an interior having an internal taper complementary to said external taper of said saddle element.

6. The implant of claim 1, wherein said arm portion is cylindrical.

7. The implant of claim 1, wherein said arm portion fits inside a pedicle screw.

\* \* \* \* \*